(12) United States Patent
Suzuki et al.

(10) Patent No.: US 6,423,048 B1
(45) Date of Patent: Jul. 23, 2002

(54) DISPOSABLE UNDERGARMENT HAVING BARRIER FLAPS

(75) Inventors: Naomi Suzuki; Yoshitaka Mishima, both of Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/539,902

(22) Filed: Mar. 31, 2000

(30) Foreign Application Priority Data

Apr. 2, 1999 (JP) .......................................... 11-096862

(51) Int. Cl.$^7$ ................................................ A61F 13/15
(52) U.S. Cl. ........................ 604/385.28; 604/385.27; 604/385.26; 604/385.01
(58) Field of Search ........................ 604/385.28, 385.26, 604/385.27, 385.01, 385.23, 855.24, 385.25

(56) References Cited

U.S. PATENT DOCUMENTS

| 3,995,637 A | 12/1976 | Schaar |
| 5,439,459 A | 8/1995 | Tanji et al. |
| 5,542,941 A | 8/1996 | Morita |
| 5,624,424 A | * 4/1997 | Saisaka et al. ........... 604/385.2 |
| 5,851,204 A | 12/1998 | Mizutani |

FOREIGN PATENT DOCUMENTS

| EP | 0 346 477 | 12/1989 |
| GB | 2 262 873 | 7/1993 |

\* cited by examiner

*Primary Examiner*—Aaron J. Lewis
*Assistant Examiner*—Jacqueline F Stephens
(74) *Attorney, Agent, or Firm*—Lowe Hauptman Gilman & Berner, LLP

(57) ABSTRACT

A disposable diaper includes barrier side flaps extending along an opposite side edges 1a of a diaper body. The barrier side flaps each includes a first side section extending above an upper side of the body and a second side section extending below a lower side of the body. The second side section includes being folded back with its inner surface put flat together so as to define a free subsection extending inward of the body and a fixed subsection extending outward of the body. A surface of the fixed subsection opposed to the lower side of the body is joined to the lower side and opposite end sections of the barrier flaps are collapsed inward of the body and joined to the upper side of the body at the opposite ends of the body.

11 Claims, 4 Drawing Sheets

DISPOSABLE UNDERGARMENT HAVING BARRIER FLAPS

BACKGROUND OF THE INVENTION

This invention relates to disposable undergarments such as diaper covers or disposable diapers.

Japanese Patent Application Disclosure No. 1996-289902 describes a disposable diaper comprising a topsheet consisting of a central sheet and side sheets provided separately of the central sheet, a backsheet, a liquid-absorbent core disposed between these sheets, and a pair of barrier flaps in the form of side sheets longitudinally extending in the outer vicinity of transversely opposite side edges of the absorbent core.

Each of the side sheets comprises a proximal portion extending longitudinally of the diaper, an inner side portion extending transversely inward from the proximal portion and an outer side portion extending transversely outward from the proximal portion. The side sheets overlap the backsheet extending transversely outward from transversely opposite side edges of the central sheet and the side sheets have their inner surfaces joined to the upper surface of the backsheet. Longitudinally opposite ends of the respective side sheets are collapsed inwardly of the diaper and have their inner surfaces bonded to the upper surface of the topsheet.

In the vicinity of a distal end of the inner side portion, an elastic member is secured under tension to the inner side portion so as to extend longitudinally of the diaper so that the elastic member contracts to rise the inner side portion of the side sheet as the diaper is longitudinally curved with its inner surface inside.

In the case of the diaper described in the Japanese Patent Application Disclosure No. 1996-289902, the inner side portion of the side sheet is apt to move toward the upper surface of the central sheet. With a disadvantageous consequence, the side sheets may be risen insufficiently to prevent excretion from leaking beyond these side sheets.

SUMMARY OF THE INVENTION

It is an object of this invention to provide a disposable undergarment improved so that the barrier side flaps may be easily risen and thereby leakage of excretion may be reliably avoided.

According to this invention, there is provided an improvement in a disposable undergarment comprising sheet members contoured by transversely opposite and longitudinally extending side edges, longitudinally opposite and transversely extending ends and a pair of barrier side flaps extending longitudinally of the sheet members along the transversely opposite side edges and normally biased to be risen on an upper side of the sheet members.

According to this invention, the improvement is in that each of the barrier side flaps comprises a first side section extending above the upper side of the sheet members longitudinally thereof, a second side section extending below a lower side of the sheet members longitudinally thereof and longitudinally opposite end sections lying on the upper side of the sheet members at the longitudinally opposite ends thereof; the second side section includes a fold which extends longitudinally of the sheet members along which the second side section is folded back with an inner surface thereof put flat together so as to define a free subsection extending inward transversely of the sheet members and a fixed subsection extending outward transversely of the sheet members; and a surface of the fixed subsection opposed to the lower side of the sheet members is joined to the lower side and the longitudinally opposite end sections are collapsed inward transversely of the sheet members and joined to the upper side of the sheet members at the longitudinally opposite ends of the sheet members.

This invention includes an embodiment as follows:

The sheet members are provided with at least one barrier end flap extending transversely of the sheet members to cover at least one of the longitudinally opposite ends of the sheet members, the barrier end flap comprising a first section extending above the upper side of the sheet members transversely of the sheet members, a second section extending below the lower side of the sheet members transversely of the sheet members, and transversely opposite end sections lying on the upper side of the sheet members at the transversely opposite ends of at least one of the longitudinally opposite ends of the sheet members, wherein the second section includes a fold extending transversely of the sheet members along which the second section is folded back with an inner surface of the second section put flat together so as to define a free subsection extending outward transversely of the sheet members and a fixed subsection extending inward transversely of the sheet members and wherein a surface of the fixed subsection opposed to the lower surface of the sheet members is joined to the lower surface and the longitudinally opposite end sections are joined to the associated ones of the longitudinally opposite ends of the barrier side flaps.

With the disposable undergarment according to this invention, the barrier side flaps are normally biased to be spaced apart from the upper surface of the panel and such a biasing effect facilitates the barrier side flaps to rise on the upper surface of the panel. The topsheet cooperates with the distal side sections of the respective barrier side flaps to form the pockets opening inwardly of the panel as the barrier side flaps are risen. In this manner, leakage of excretion which would otherwise occur along the transversely opposite side edges of the panel can be reliably avoided.

With the disposable undergarment according to this invention which is additionally provided with a pair of the end flaps, the barrier end flaps also are normally biased to be spaced apart from the upper surface of the panel.

Consequently, such a biasing effect facilitates these barrier end flaps to rise on the upper surface of the panel. The topsheet cooperates with the distal sections of the respective barrier end flaps to form the pockets opening inwardly of the panel as the barrier end flaps are risen. In this manner, leakage of excretion which would otherwise occur along the transversely opposite side edges as well as along the longitudinally opposite ends of the panel can be reliably avoided.

DETAILED DESCRIPTION OF THE PREFERRED EMBODIMENTS

Details of a disposable undergarment according to this invention will be more fully understood from the description of open type disposable diaper given hereunder as one embodiment with reference to the accompanying drawings.

Figure 1:
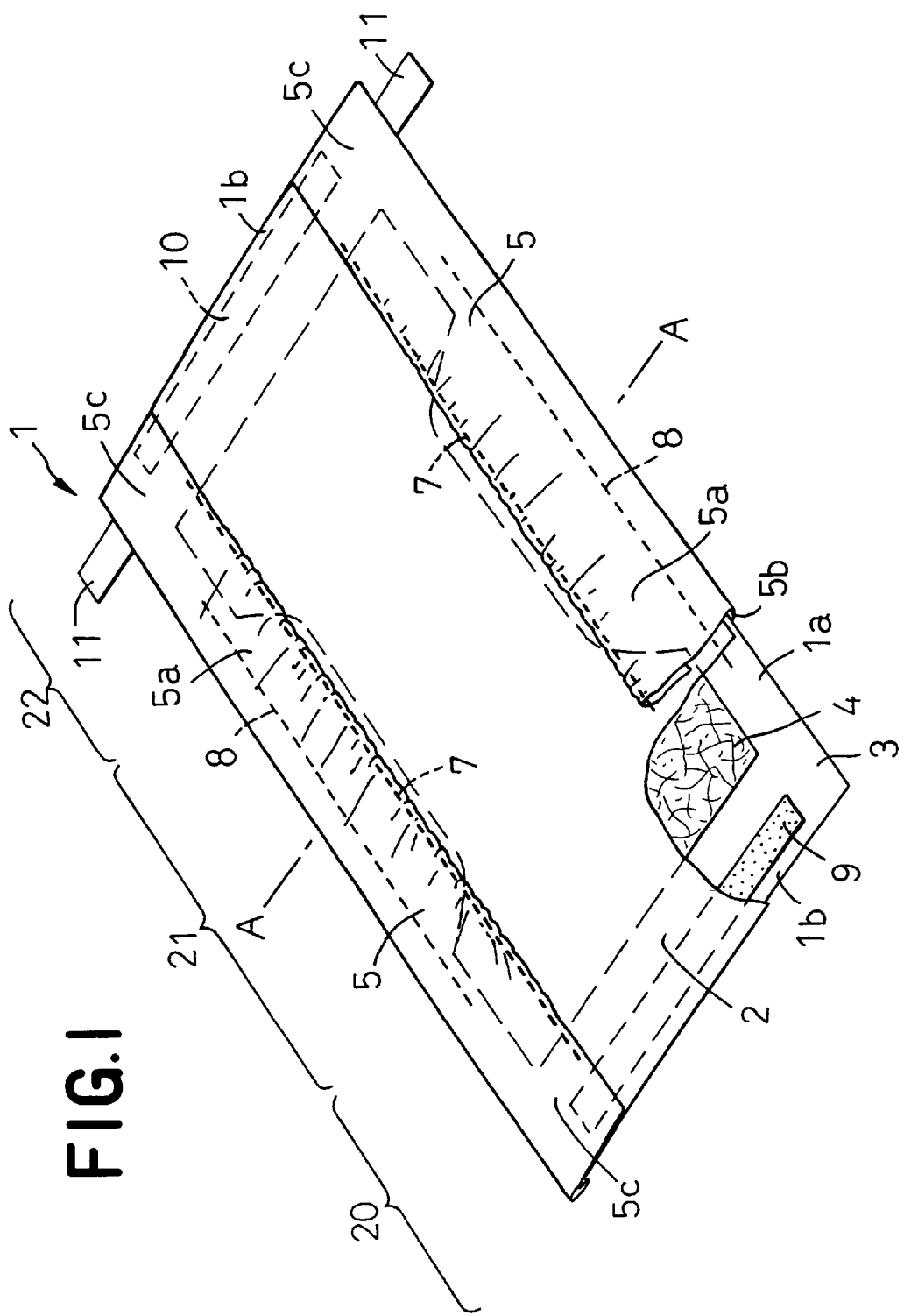
FIG. 1 is a partially cutaway perspective view showing one embodiment of diaper according to this invention.
Figure 2:
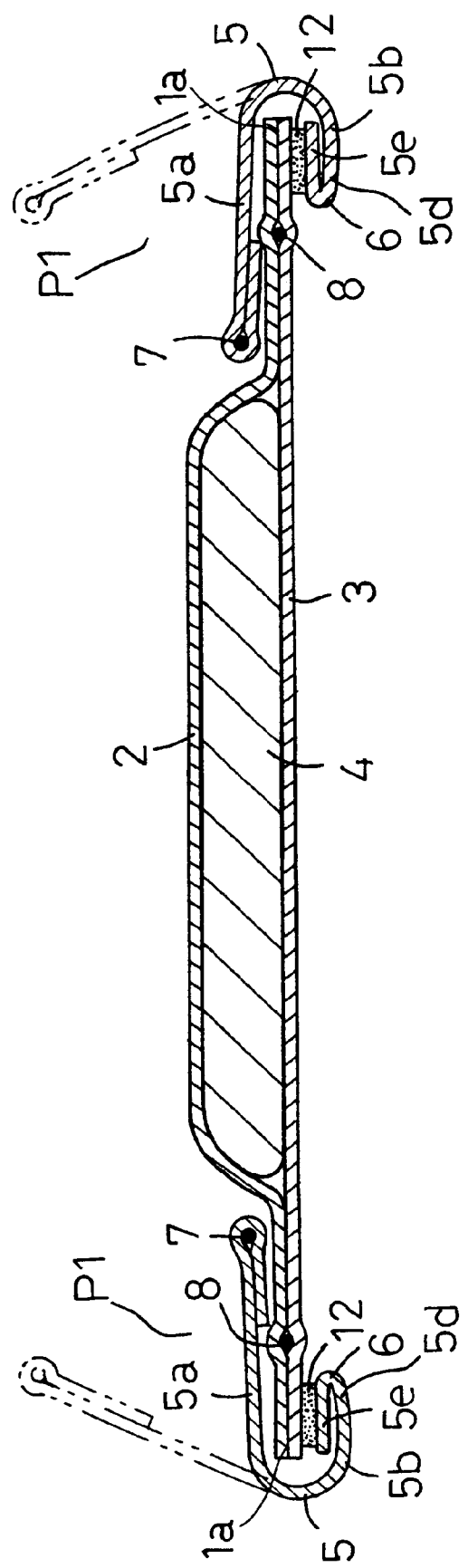
FIG. 2 is a sectional view taken along line A—A in FIG. 1.

FIG. 1 is a partially cutaway perspective view showing diaper comprising a laminate panel 1 and FIG. 2 is a sectional view taken along line A—A in FIG. 1. Referring to FIG. 2, a pair of barrier side flaps 5 are illustrated by imaginary lines at their risen positions. The panel 1 comprises a liquid-pervious topsheet 2, a liquid-impervious backsheet 3 underlying the topsheet 2 and a liquid-absorbent core 4 disposed between these topsheet 2 and the backsheet 3 and joined to the inner surface of at least one of these topsheet 2 and backsheet 3. Contoured by transversely opposite and longitudinally extending side edges 1a and longitudinally opposite and transversely extending ends 1b, the panel 1 has a front waist region 20, a rear waist region 22 and a crotch region 21 extending between these front and rear waist regions 20, 22 as viewed longitudinally of the panel 1. Along the side edges 1a, the pair of barrier side flaps 5 provided with elastic members 7 secured under tension thereto extend longitudinally of the panel 1.

Each of the barrier side flaps 5 is made of a nonwoven fabric and extends on the upper surface of the panel 1 longitudinally of the panel 1. The barrier side flap 5 comprises a distal side section 5a extending longitudinally of the panel 1 above the upper surface of the panel 1 and, in the crotch region 21, joined neither to the topsheet 2 nor to the backsheet 3, a proximal side section 5b extending longitudinally of the panel 1 below the lower surface of the panel 1, and longitudinally opposite ends sections 5c extending on the upper surface of the panel 1 at the longitudinally opposite ends 1b thereof.

The proximal side section 5b of the barrier side flap 5 includes a fold 6 extending longitudinally of the panel 1, along which the proximal side section 5b is folded back so that the inner surface of the proximal side section 5b may be put flat together. The proximal side section 5b comprises a free subsection 5d extending transversely inward from the side edge 1a of the panel 1 and a fixed subsection 5e extending transversely outward from the fold 6. A surface of the subsection 5e opposed to the lower surface of the backsheet 3 is joined to this lower surface by means of adhesive agent 12. The distal side section 5a is folded inwardly of the panel 1 and wraps the elastic member 7 secured under tension to the barrier side flap 5. The longitudinally opposite end sections 5c have their inner surfaces joined to the upper surface of the topsheet 2 so as to be held in their positions collapsed inwardly of the panel 1.

The free subsection 5d and the fixed subsection 5e are biased to restore their initial positions at which they define a single plane including the fold 6. Such biasing effect causes the distal side section 5a to move away from the upper surface of the panel 1 and thereby facilitates the barrier side flap 5 to rise on the upper surface of the panel 1.

As indicated by the imaginary lines in FIG. 2, the elastic member 7 contracts to rise the barrier side flap 5 as the panel 1 is longitudinally curved with its inner surface inside. As a result, the distal side section 5a of the flap 5 and the topsheet 2 form a pocket P1 opening inwardly of the panel 1.

The free subsection 5d is joined neither to the backsheet 3 nor to the joined subsection 5e and therefore a height by which the barrier side flap 5 can be risen substantially corresponds to a length of the distal side section 5a plus a length of the free subsection 5d as measured transversely of the panel 1. Accordingly, even if the panel 1 is spaced apart from the wearer's skin by the length of the distal side section during actual use of the diaper, the length of the free subsection 5d can compensate this and thereby maintain a desired fit of the barrier side flap 5 around the wearer's leg.

In the panel 1, the distal side section 5a of the barrier side flap 5 and the free subsection 5d of the proximal side section 5b function as a barrier and the pocket P1 functions to receive excretion exuding out from the absorbent core 4. In this manner, leakage of excretion which would otherwise occur along the transversely opposite side edges 1a of the panel 1 is reliably avoided.

The front and rear waist regions 20, 22 are provided along the longitudinally opposite ends 1b of the panel 1 with film-like elastic members 9, 10 extending transversely of the panel 1. These elastic members 9, 10 associated with a waist-opening are disposed between the topsheet 2 and the backsheet 3 and secured under tension to at least one of these sheets 2, 3.

The crotch region 21 is provided along the transversely opposite side edges 1a of the panel 1 with elastic members 8 extending longitudinally of the panel 1 in association with respective leg-openings. These elastic members 8 are disposed between the topsheet 2 and the backsheet 3 and secured under tension to at least one of these sheets 2, 3.

These elastic members 8 lie below the distal side sections 5a of the respective barrier side flaps 5 and are pressed against the wearer's legs with interposition of the respective distal side sections 5a.

The rear waist region 22 is provided with a pair of tape fasteners 11 having their proximal ends attached thereto so that these tape fasteners 11 extending transversely outward from the transversely opposite side edges 1a of the panel 1. FIG. 1 illustrates a state in which these elastic members 7, 8, 9, 10 are slightly relaxed and gathers are formed along the longitudinally opposite ends 1b of the panel 1, along the transversely opposite edges of the panel 1 in the crotch region 21 and along the distal side section 5a of the flap 5.

Figure 3:
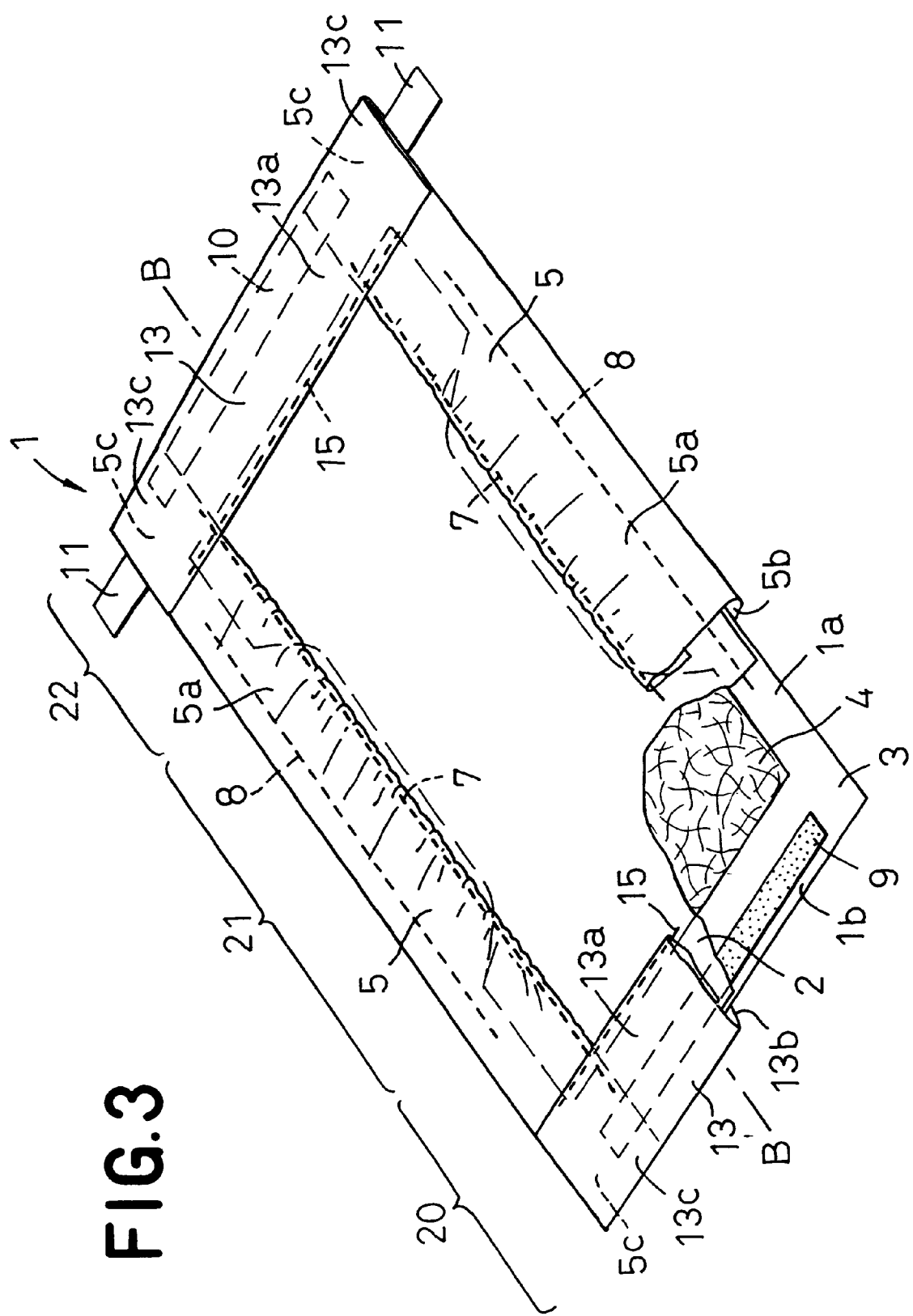
FIG. 3 is a view similar to FIG. 1 showing another embodiment of diaper according to this invention.
Figure 4:
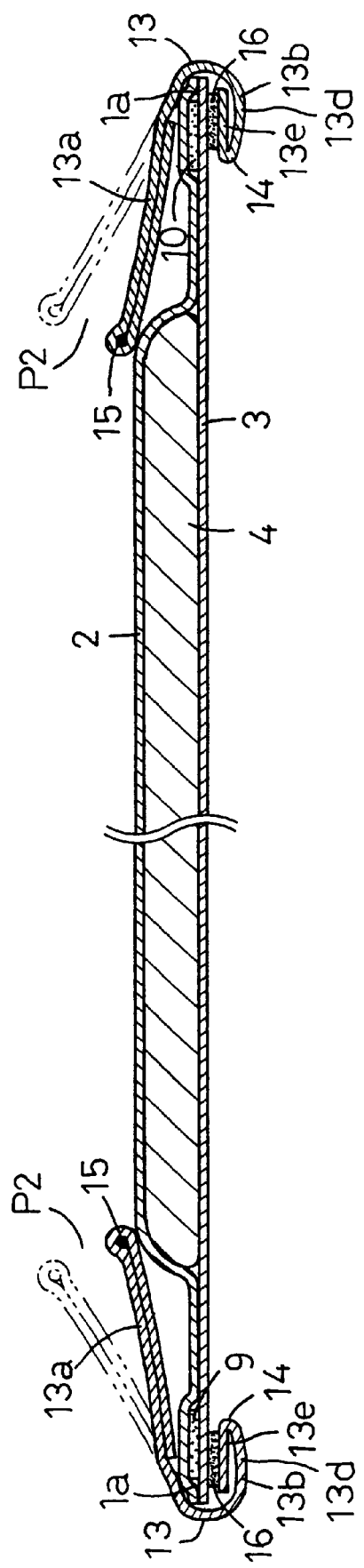
FIG. 4 is a sectional view taken along line B—B in FIG. 3.

FIG. 3 is a partially cutaway perspective view showing the panel 1 according to an embodiment different from the panel 1 of FIG. 1 and FIG. 4 is a sectional view taken along line B—B in FIG. 3. Referring to FIG. 4, a pair of barrier end flaps 13 are illustrated by imaginary lines in their risen positions. The panel 1 according to this alternative embodiment is similar to the panel 1 shown by FIG. 1 in that it comprises the topsheet 2, the backsheet 3 and the absorbent core 4 disposed between these two sheets 2, 3 and also in that the panel 1 is provided along its transversely opposite side edges 1a with a pair of the longitudinally extending barrier side flaps 5, respectively.

The panel 1 is provided along the longitudinally opposite ends 1b with a pair of the barrier end flap 13 extending transversely of the panel 1 and covering the longitudinally opposite ends 1b. Each of the barrier end flaps 13 is made of a nonwoven fabric and comprises a distal section 13a extending above the upper surface of the panel 1 and, between the end sections 5c of the barrier side flaps 5 overlapping transversely opposite ends of this barrier end flap 13, joined neither to the topsheet 2 nor to the backsheet 3, a section 13b extending transversely of the panel 1 below the panel 1, and transversely opposite end sections 13c overlapping the associated one of the longitudinal ends 1b above the panel 1. The barrier end flap 13 is provided with an elastic member 15 secured under tension thereto.

The proximal section 13b of the barrier end flap 13 includes a fold 14 extending transversely of the panel 1, along which the proximal section 13b is folded back so that the inner surface of the proximal section 13b may be put flat together. The proximal section 13b comprises a free subsection 13d extending longitudinally inward from the longitudinal end 1b of the panel 1 and a fixed subsection 13e extending longitudinally outward from the fold 14. A surface of the subsection 13e opposed to the lower surface of the backsheet 3 is joined to this lower surface by means of adhesive agent 16. The distal section 13a is folded inwardly of the panel 1 and wraps the elastic member 15 secured under tension to the barrier end flap 13. The transversely opposite end sections 13c have their inner surfaces bonded to the upper surface of the longitudinal ends of the barrier side flap 5 so as to be held in their positions placed upon the upper surfaces of the respective longitudinal ends 5c of the barrier side flaps 5.

The free subsection 13d and the fixed subsection 13e are biased to restore their initial positions at which they define a single plane including the fold 16. Such biasing effect causes the distal section 13a to move away from the upper surface of the panel 1 and thereby facilitates the barrier end flap 13 to rise on the upper surface of the panel As indicated by the imaginary lines in FIG. 4, the barrier end flap 13 rises on the panel 1 as the elastic member 15 contracts and the section 13a and the topsheet 2 form a pocket P3 opening inwardly of the panel 1.

The free subsection 13d is joined neither to the backsheet 3 nor to the joined subsection 13e and therefore a height by which the barrier end flap 13 can be risen substantially corresponds to a length of the distal section 13a plus a length of the free subsection 13d as measured longitudinally of the panel 1. Accordingly, even if the panel 1 is spaced apart from the wearer's skin by the length of the distal section 13a during actual use of the diaper, the length of the free subsection 13d can compensate this and thereby maintain a desired fit of the barrier end flap 13 to the wearer's skin.

In the panel 1, the sections 5a, 5d of the flap 5 cooperate with the sections 13a, 13d of the barrier end flap 13 to function as a barrier and the pockets P1, P2 function to receive excretion exuding out from the absorbent core 4. In this manner, leak of excretion which would otherwise occur along the transversely opposite side edges 1a and the longitudinally opposite ends 1b of the panel 1 is reliably avoided.

The topsheet 2 is made of a liquid-pervious sheet, preferably of a liquid-pervious and hydrophobic sheet such as a nonwoven fabric or a porous plastic film. The backsheet 3 is made of a liquid-impervious plastic film or a laminate sheet of plastic film and a hydrophobic nonwoven fabric, preferably of a breathable and liquid-impervious sheet.

The barrier side flaps 5 as well as the barrier end flaps 13 are made of a breathable and liquid-impervious nonwoven fabric or a breathable and stretchable nonwoven fabric. When the stretchable nonwoven fabric is used, the barrier side flaps 5 and the barrier end flaps 13 are joined under tension to the panel 1 and it is unnecessary to provide the distal side sections 5a of the respective barrier side flaps 5 as well as the distal sections 13a of the respective barrier end flaps 13 with the elastic members 7, 15.

The nonwoven fabric may be selected from a group including nonwoven fabrics of various types such as spun lace-, needle punch-, melt blown-, thermal bond-, spun bond- and chemical bond-types. The nonwoven fabric should have a basis weight of 15~80 $g/m^2$, preferably of 20~60 $g/m^2$. Component fibers of the nonwoven fabric may be, for example, polyolefine, polyester or polyamide, or conjugate fibers of polyethylene/polypropylene or polyester.

The absorbent core 4 basically comprises a compressed mixture of fluff pulp and superabsorptive hydrogel particles entirely covered with a water-pervious sheet such as tissue paper. Fixing of these sheets 2, 3, 5, 13 and securing of the elastic members 7, 8, 9, 10, 15 may be achieved by using, in addition to a suitable adhesive agent such as a hot melt adhesive agent or glue, a heat-sealing technique.

This invention is applicable not only to the open type disposable diaper but also to diaper cover made of a liquid-impervious plastic film or a laminate of such plastic film and a hydrophobic nonwoven fabric.

What is claimed is:

1. A disposable undergarment, comprising:

sheet members contoured by transversely opposite and longitudinally extending side edges, longitudinally opposite and transversely extending ends; and a pair of barrier side flaps extending longitudinally of said sheet members along said transversely opposite side edges and being biased to rise from an upper side of said sheet members;

each of said barrier side flaps comprising a first side section extending longitudinally and above the upper side of said sheet members, and a second side section extending longitudinally and below a lower side of said sheet members, longitudinally opposite ends of each of said barrier side flaps being collapsed inward transversely of said sheet members and joined to the upper side of said sheet members at the longitudinally opposite ends of said sheet members;

said second side section comprising a first fold which extends longitudinally of said sheet members and divides said second side section into a first free subsection extending inward from the first side section and transversely of said sheet members, and a first fixed subsection extending outward from the first free subsection and transversely of said sheet members, said first free and fixed subsections overlying each other; and said first fixed subsection being joined to a lower side of said sheet members.

2. The disposable undergarment according to claim 1, wherein each of said barrier side flap is made of a nonwoven fabric and provided along said first side section with at least one elastic member secured under tension to said first side section so as to extend longitudinally of said sheet members.

3. The disposable undergarment according to claim 1, wherein each of said barrier side flap is made of a stretchable nonwoven fabric and joined under tension to said sheet members so as to extend longitudinally of said sheet members.

4. The disposable undergarment according to claim 1, further comprising at least one barrier end flap extending transversely of said sheet members to cover at least one of the longitudinally opposite ends of said sheet members;

said barrier end flap comprising a first section extending above the upper side of said sheet members transversely of said sheet members, and a second section extending below the lower side of said sheet members transversely of said sheet members, transversely opposite ends said barrier end flap lying on the upper side of said sheet members and being bonded to the respectively longitudinally opposite ends of said barrier side flaps;

said second section comprising a second fold which extends transversely of said sheet members and divides said second section into a second free subsection extending inward from the first section and longitudinally of said sheet members, and a second fixed subsection extending outward from the second free subsection and longitudinally of said sheet members, said second free and fixed subsections overlying each other; and said second fixed subsection being joined to the lower side of said sheet members.

5. The disposable undergarment according to claim 4, wherein said barrier end flap is made of a nonwoven fabric and provided with at least one elastic member secured under tension to said first section so as to extend transversely of said sheet members.

6. The disposable undergarment according to claim 4, wherein said barrier end flap is made of a stretchable nonwoven fabric and joined under tension to said sheet members so as to extend transversely thereof.

7. The disposable undergarment according to claim 1, wherein said disposable undergarment is a disposable diaper comprising a laminate panel comprising said sheet members which include a liquid-pervious topsheet and a liquid-impervious backsheet of said laminate panel, said laminate panel further comprising a liquid-absorbent core disposed between the topsheet and the backsheet;

wherein said first fixed subsections of said barrier side flaps are joined to a lower surface of said backsheet; and said longitudinally opposite ends of said barrier side flaps are joined to an upper surface of said topsheet.

8. The disposable undergarment according to claim 7, wherein said laminate panel is provided, in the vicinity of said transversely opposite and longitudinally extending side edges, with elastic members secured under tension to said laminate panel so as to extend longitudinally of said laminate panel.

9. The disposable undergarment according to claim 7, wherein said barrier side flaps are not joined to said topsheet in a crotch region of said laminate panel located between said longitudinally opposite and transversely extending ends.

10. The disposable undergarment according to claim 4, wherein said disposable undergarment is a disposable diaper comprising a laminate panel comprising said sheet members which include a liquid-pervious topsheet and a liquid-impervious backsheet of said laminate panel, said laminate panel further comprising a liquid-absorbent core disposed between the topsheet and the backsheet;

wherein said first fixed subsections of said barrier side flaps and said fixed subsection of said at least one barrier end flap are joined to a lower surface of said backsheet; and said longitudinally opposite ends of said barrier side flaps are joined to an upper surface of said topsheet.

11. The disposable undergarment according to claim 10, wherein said at least one barrier end flaps is not joined to said topsheet in a region between said bondings to the associated one of said longitudinally opposite ends of each of said barrier side flaps.

* * * * *